(12) United States Patent
Sobe et al.

(10) Patent No.: US 8,862,204 B2
(45) Date of Patent: *Oct. 14, 2014

(54) REDUCING MECHANICAL STRESS ON CONDUCTORS AND CONNECTION POINTS IN A POSITION DETERMINABLE INTERVENTIONAL MEDICAL DEVICE

(75) Inventors: Lior Sobe, Kadima (IL); Ran Sela, Tel Aviv-Yafo (IL)

(73) Assignee: MediGuide Ltd., Haifa (IL)

(*) Notice: Subject to any disclaimer, the term of this patent is extended or adjusted under 35 U.S.C. 154(b) by 846 days.

This patent is subject to a terminal disclaimer.

(21) Appl. No.: 12/982,592

(22) Filed: Dec. 30, 2010

(65) Prior Publication Data

US 2011/0118592 A1 May 19, 2011

Related U.S. Application Data

(63) Continuation-in-part of application No. 10/408,156, filed on Apr. 7, 2003, now Pat. No. 7,881,769, which is a continuation of application No. 10/298,358, filed on Nov. 18, 2002, now abandoned.

(51) Int. Cl.
| | |
|---|---|
| A61B 5/05 | (2006.01) |
| A61B 17/3207 | (2006.01) |
| A61B 18/14 | (2006.01) |
| A61N 7/02 | (2006.01) |
| A61M 29/02 | (2006.01) |
| A61B 19/00 | (2006.01) |
| A61B 17/00 | (2006.01) |
| A61B 18/24 | (2006.01) |

(52) U.S. Cl.
CPC .......... *A61B 17/3207* (2013.01); *A61B 18/1492* (2013.01); *A61N 7/022* (2013.01); *A61M 29/02* (2013.01); *A61B 2019/5272* (2013.01); *A61B 19/5244* (2013.01); *A61B 2019/5251* (2013.01); *A61B 2017/00252* (2013.01); *A61B 18/24* (2013.01)
USPC .......... 600/424; 600/407; 600/479; 600/481; 600/488; 604/508; 604/510; 604/522

(58) Field of Classification Search
USPC .......... 600/424, 479, 481–488; 604/508–522
See application file for complete search history.

(56) References Cited

U.S. PATENT DOCUMENTS

| | | |
|---|---|---|
| 5,489,271 A | 2/1996 | Andersen |
| 5,588,432 A | 12/1996 | Crowley |

(Continued)

FOREIGN PATENT DOCUMENTS

| | | |
|---|---|---|
| WO | WO96005768 | 2/1996 |
| WO | WO-97/29684 | 8/1997 |

(Continued)

OTHER PUBLICATIONS

International Search Report issued in International (PCT) Patent Application No. PCT/IL03/00940 (Feb. 28, 2006).

(Continued)

*Primary Examiner* — Unsu Jung
*Assistant Examiner* — Joel Lamprecht
(74) *Attorney, Agent, or Firm* — Dykema Gossett PLLC

(57) ABSTRACT

A medical device configured for diagnosis or treatment of tissues within a body is provided. The device includes an elongate, deformable member configured to be received within a lumen in the body and having proximal and distal ends. A position sensor is disposed at the distal end. In one embodiment, a conductor is wound about the member. The conductor is connected to the position sensor and has a first winding pitch over a first portion of the deformable member and a second winding pitch, different from the first winding pitch, over a second portion of the deformable member. In another embodiment, the member defines a neutral longitudinal axis extending between the proximal and distal ends. A conductor extending between the proximal and distal ends is connected to the position sensor at a connection node on the neutral axis.

20 Claims, 4 Drawing Sheets

(56) References Cited

U.S. PATENT DOCUMENTS

| | | | |
|---|---|---|---|
| 5,646,525 | A | 7/1997 | Gilboa |
| 5,830,222 | A | 11/1998 | Makower |
| 5,840,024 | A | 11/1998 | Taniguchi et al. |
| 5,873,835 | A | 2/1999 | Hastings et al. |
| 5,897,529 | A | 4/1999 | Ponzi |
| 5,916,241 | A | 6/1999 | Rudie et al. |
| 5,928,248 | A | 7/1999 | Acker |
| 6,035,856 | A | 3/2000 | LaFontaine et al. |
| 6,179,811 | B1 | 1/2001 | Fugoso et al. |
| 6,203,493 | B1 | 3/2001 | Ben-Haim |
| 6,231,516 | B1 | 5/2001 | Keilman et al. |
| 6,233,476 | B1 | 5/2001 | Strommer et al. |
| 6,251,107 | B1 | 6/2001 | Schaer |
| 6,253,770 | B1 | 7/2001 | Acker et al. |
| 6,298,259 | B1 | 10/2001 | Kucharczyk et al. |
| 6,427,079 | B1 | 7/2002 | Schneider et al. |
| 6,509,521 | B1 | 1/2003 | Geitz |
| 6,618,612 | B1 | 9/2003 | Acker et al. |
| 6,689,049 | B1 | 2/2004 | Miyagi et al. |
| 6,690,963 | B2 | 2/2004 | Ben-Haim et al. |
| 7,881,769 | B2 * | 2/2011 | Sobe ............................. 600/424 |
| 2002/0016589 | A1 | 2/2002 | Swartz et al. |
| 2002/0099364 | A1 | 7/2002 | Lalonde |
| 2002/0128537 | A1 | 9/2002 | Watanabe et al. |
| 2002/0143371 | A1 | 10/2002 | Balczewski et al. |
| 2004/0097804 | A1 | 5/2004 | Sobe |
| 2007/0225641 | A1 | 9/2007 | Schneider et al. |

FOREIGN PATENT DOCUMENTS

| | | |
|---|---|---|
| WO | WO-98/10303 | 3/1998 |
| WO | WO 98/52637 | 11/1998 |
| WO | WO 99/39624 | 8/1999 |
| WO | WO 99/59479 | 11/1999 |
| WO | WO-00/10456 | 3/2000 |
| WO | WO-00/16684 | 3/2000 |

OTHER PUBLICATIONS

"PTCA with Stent" http://www.bostonscientific.com/common_templates/articleDisplayTemplate.jhtml?task=tskProcedureOverview.jhtml&sectionID=4&relid=2,63,64&procedureId=94.

Kern, Morton J., "The Interventional Cardiac Catheterization Handbook," 3rd ed., Mosby-Year Book, Inc. pp. 17-43, 72-74, 80-101, 224-250, 393 and 436 (1999).

* cited by examiner

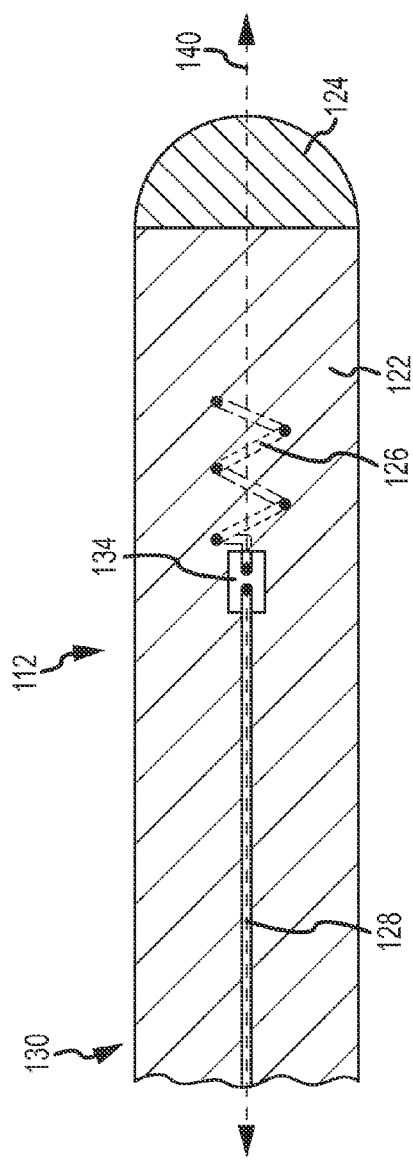
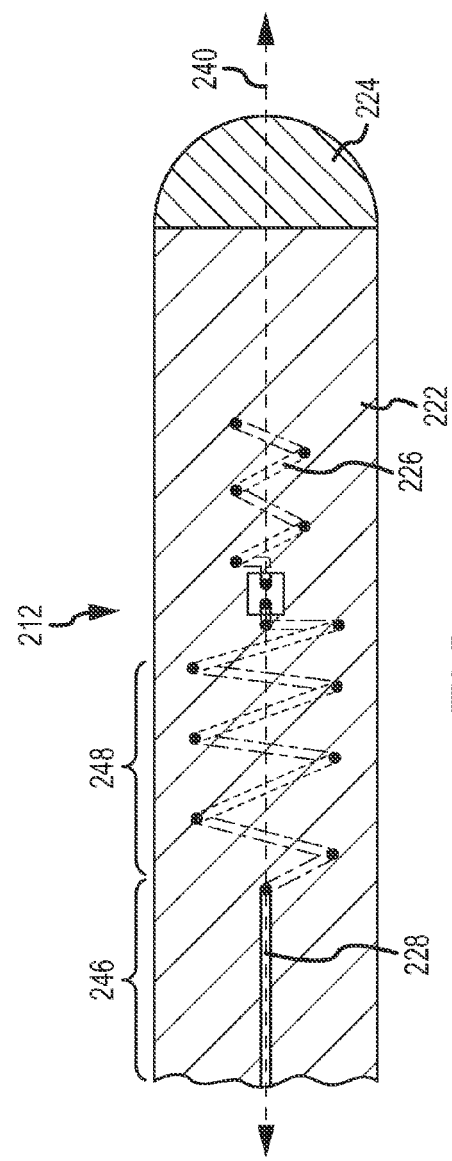

REDUCING MECHANICAL STRESS ON CONDUCTORS AND CONNECTION POINTS IN A POSITION DETERMINABLE INTERVENTIONAL MEDICAL DEVICE

The present application is a continuation-in-part of U.S. patent application Ser. No. 10/408,156, filed Apr. 7, 2003, now U.S. Pat. No. 7,881,769, issued 1 Feb. 2011, which is a continuation of U.S. patent application Ser. No. 10/298,358 filed Nov. 18, 2002, now abandoned. Each application referenced in this paragraph is incorporated herein by reference in its entirety.

BACKGROUND OF THE INVENTION a. Field of the Invention

This invention relates to a medical device for treatment and diagnosis of tissues within a body. In particular, the invention relates to a device in which mechanical stress on conductors carrying signals from position sensors on the device and at the connection point of the conductors to the sensors may be reduced.

b. Background Art

It is desirable to track the position of medical devices such as catheters as they are moved within a body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and clinician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device. The information derived from these systems is then provided to a clinician through, for example, a visual display.

The position sensors are typically located at or near a distal end of the medical device. The sensors generate signals indicative of the position of the distal end of the medical device. Conductors are connected to the position sensors and carry the signals from the position sensors to an electronic control unit that is typically disposed outside of the body at the proximal end of the medical device. As the medical device is maneuvered through the body to and from a region of interest, these conductors—and the points of connection between the conductors and the position sensors—are subjected to mechanical stress.

The inventors herein have recognized a need for a medical device for treatment and diagnosis of tissues within a body that will minimize and/or eliminate one or more of the above-identified deficiencies.

BRIEF SUMMARY OF THE INVENTION

It is desirable to provide a medical device for treatment and diagnosis of tissues within a body a system. In particular, it is desirable to provide a medical device that reduces mechanical stress on conductors carrying signals from position sensors on the device and at the connection point of the conductors to the sensors.

A medical device configured for diagnosis or treatment of a tissue within a body in accordance with one embodiment of the invention includes an elongate, deformable member configured to be received within a lumen in the body. The deformable member has a proximal end and a distal end. The device further includes a position sensor disposed at the distal end of the deformable member. The device further includes a conductor wound about the deformable member. The conductor is connected to the position sensor at a connection node. The conductor has a first winding pitch over a first portion of the deformable member and a second winding pitch over a second portion of the deformable member, the second winding pitch different from the first winding pitch.

A medical device configured for diagnosis and treatment of tissue within a body in accordance with another embodiment of the invention includes an elongate, deformable member configured to be received within a lumen in the body. The deformable member has a proximal end and a distal end. The deformable member defines a neutral longitudinal axis extending between the proximal and distal ends. The device also includes a position sensor disposed at the distal end of the deformable member and a conductor extending between the proximal and distal ends of the deformable members. The conductor is connected to the position sensor at a connection node on the neutral axis.

A medical device in accordance with the above-described embodiments of the present invention is advantageous because the devices reduce mechanical stress on the conductors and/or the connection point between the conductor and the position sensor. As a result, the device is less likely to experience damage during assembly and operation of the device and is more reliable.

The foregoing and other aspects, features, details, utilities and advantages of the present invention will be apparent from reading the following description and claims, and from reviewing the accompanying drawings.

BRIEF DESCRIPTION OF THE DRAWINGS

FIG. 4 is a cross-sectional view of a medical device in accordance with another embodiment of the present teachings.

FIG. 5 is a cross-sectional view of a medical device in accordance with another embodiment of the present teachings.

DETAILED DESCRIPTION OF EMBODIMENTS OF THE INVENTION

Figure 1:
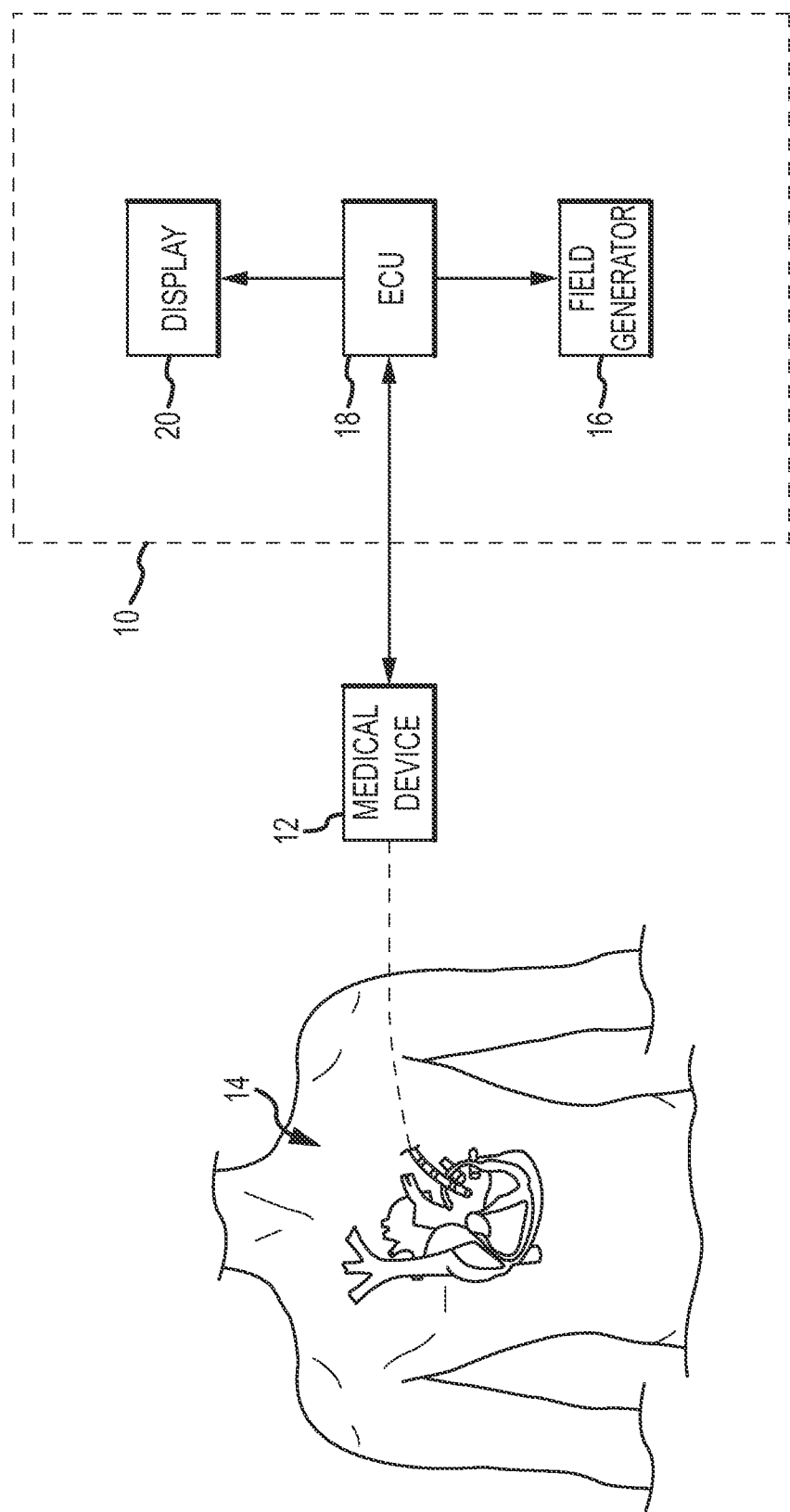
FIG. 1 is a diagrammatic view of a medical device position and navigation system.

Referring now to the drawings wherein like reference numerals are used to identify identical components in the various views, FIG. 1 illustrates a medical device position and navigation system 10. System 10 is provided to determine the position of a medical device 12 within a body 14 and to allow a clinician to navigate device 12 within body 14. System 10 is conventional in the art and includes a field generator 16, an electronic control unit 18 and a display 20.

Filed generator 16 is provided to generate electric and/or magnetic fields for the purpose of inducting changes in current and voltage on position sensors on medical device 12. In one embodiment of the invention, field generator 16 is a magnetic field generator such as that sold under the trademark "gMPS" by Mediguide, Ltd. The generator may include, for example, three orthogonally arranged coils, arranged to create a magnetic field within body 14 and to control the strength, orientation and frequency of the field. The magnetic field generator may be located above or below the patient (e.g., under a patient table) or in another appropriate location. In an alternative embodiment, the field generator 16 may comprise an electric field generator as in the system sold under the trademark "ENSITE NAVX" by St. Jude Medical, Inc. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. Magnetic fields are generated by the coils of the magnetic field generator or sinusoidal currents are driven through each pair of patch electrodes in the electric field generator and current or voltage measurements for one or more position sensors associated with the medical device 12 are obtained. The measured currents or voltages are proportional to the distance of the sensors from the coils or patch electrodes thereby allowing a position of the sensors within the coordinate system of the navigation system 10 to be determined.

Electronic control unit (ECU) 18 is provided to determine a position of the sensors within a coordinate system of the position and navigation system 10 responsive to signals generated by position sensors on device 12. ECU 18 is further provided to generate an indication of the position and orientation on display 20 by, for example, retrieving images of a region of interest from an image database having the same position and orientation coordinates within the coordinate system of system 10 and superimposing a representation of device 12 on the image at the detected position and orientation within the image. ECU 18 may also provide operational control over device 12. ECU 18 may comprise a programmable microprocessor or microcontroller or may comprise an application specific integrated circuit (ASIC). ECU 18 may include a central processing unit (CPU) and an input/output (I/O) interface through which ECU 18 may receive a plurality of input signals including signals generated by device 12 (and particularly the position sensors on device 12) and generate a plurality of output signals including those used to control and/or provide data to device 12 and display 20.

Display 20 is provided to convey information to a clinician to assist in diagnosis and treatment. Display 20 may comprise a conventional computer monitor or other display device. Display 20 presents a graphical user interface (GUI) to the physician. The GUI may include a variety of information including, for example, images of a region of interest in body 14, electrophysiological data, graphs illustrating voltage levels over time for various sensors and images of device 12.

Figure 6:
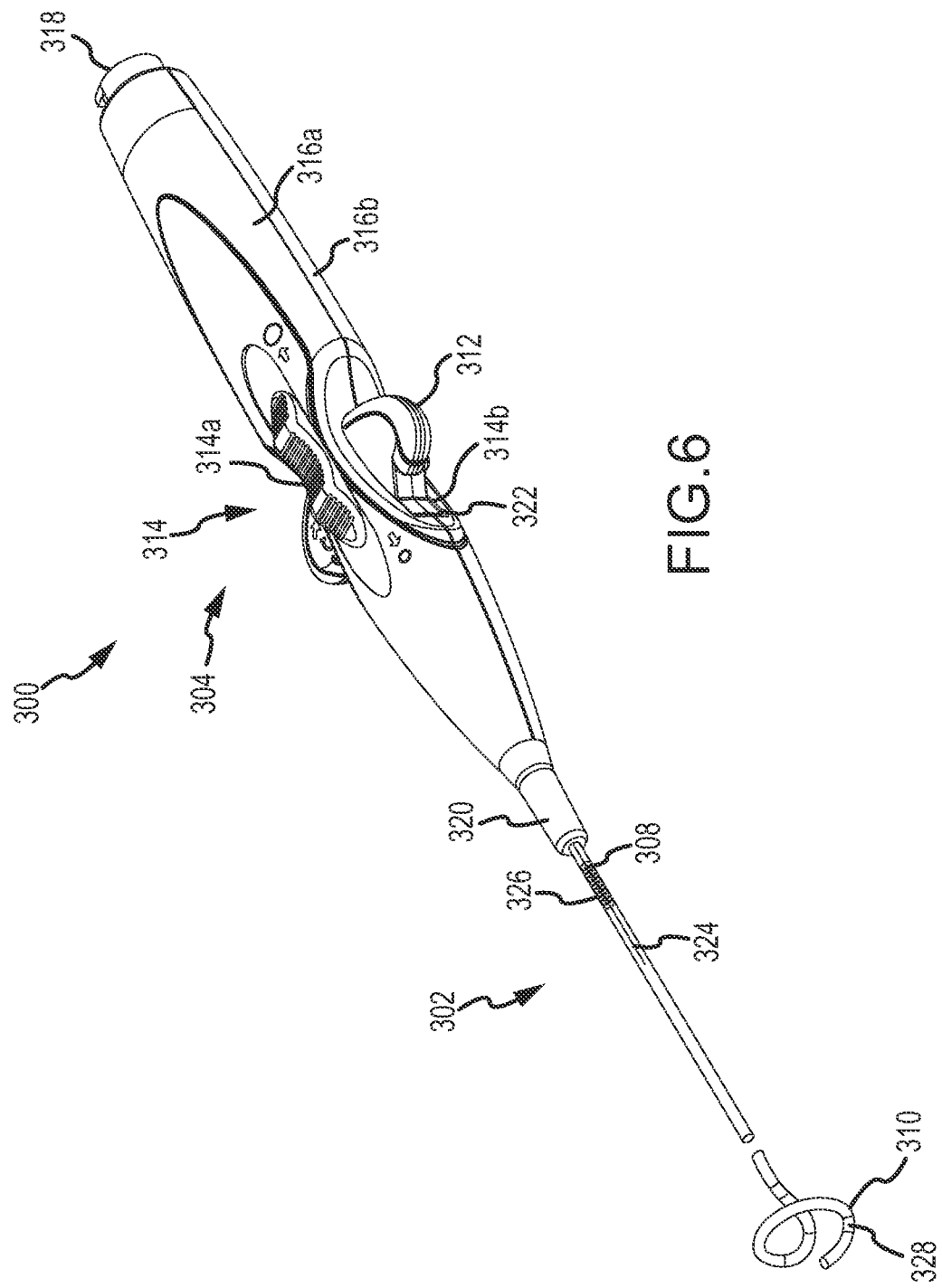
FIG. 6 is an isometric view of a particular medical device—a catheter—in accordance with the present teachings.

Referring now to FIG. 6, one exemplary medical device 12 comprises a catheter 300. Catheter 300 includes an elongate deformable member 302 and an ergonomically shaped actuation handle 304 coupled to a proximal end 308 of member 302. Handle 304 is adapted to control the deflection of a deflectable distal end 310 of member 302.

Handle 304 can include a first actuator 312, upper and lower buttons 314a, 314b of a second actuator 314, upper and lower grip portions 316a, 316b, an electrical plug 318 at the proximal end of the handle 304, and a strain relief 320 at the distal end of the handle 304. The upper and lower grip portions 316a, 316b define a space 322 that extends laterally through the grip portions 316a, 316b. The first actuator 312 is pivotally coupled to the grip portions 316a, 316b and resides in the space 322. The first actuator 312 may pivotally displace laterally relative to the grip portions 316a, 316b through the space 322. Such pivotal displacement of the first actuator 312 allows a user to bi-directionally deflect the distal end 310 of the member 302.

The upper and lower buttons 314a, 314b of the second actuator are slideably coupled to their respective grip portions 316a, 316b in such a manner that they may slideably displace along their respective grip portions 316a, 316b in a direction that is generally parallel to the longitudinal axis of the handle 304. Such slideable displacement of the buttons 314a, 314b of the second actuator 314 allows a user to deflect the distal end 310 of member 302 in a third direction. For example, as indicated in FIG. 6, in one embodiment where the distal end 310 forms a loop or lariat, the first actuator 312 causes the distal end 310 to deflect bi-directionally right or left, and the buttons 314a, 314b of the second actuator 314 cause the distal end 314 to increase or decrease the diameter of its loop or lariat. The actuation wires 324 coupled to actuators 312, 314 can be any of the actuation wire types known in the art and may comprise pull or tension wires. The actuation wires 324 can be formed from a super elastic Nitinol wire or another suitable material and may be housed within a compression coil 326 in a proximal portion of member 302. Although catheter 300 has been described with a particular handle 304 and actuators 312, 314, it should be understood that the invention as described herein can be used with any conventional handle and actuator structure.

As illustrated in FIG. 6, the distal end 310 of member 302 can include a plurality of spaced position sensors 328. Each sensor 328 is connected to conductor that extends to the electrical plug 318 through member 302, the strain relief 320, and the handle 304. The electrical plug 318 is adapted to be connected to a device, such as a recording, monitoring, or ablation device.

Figure 2:
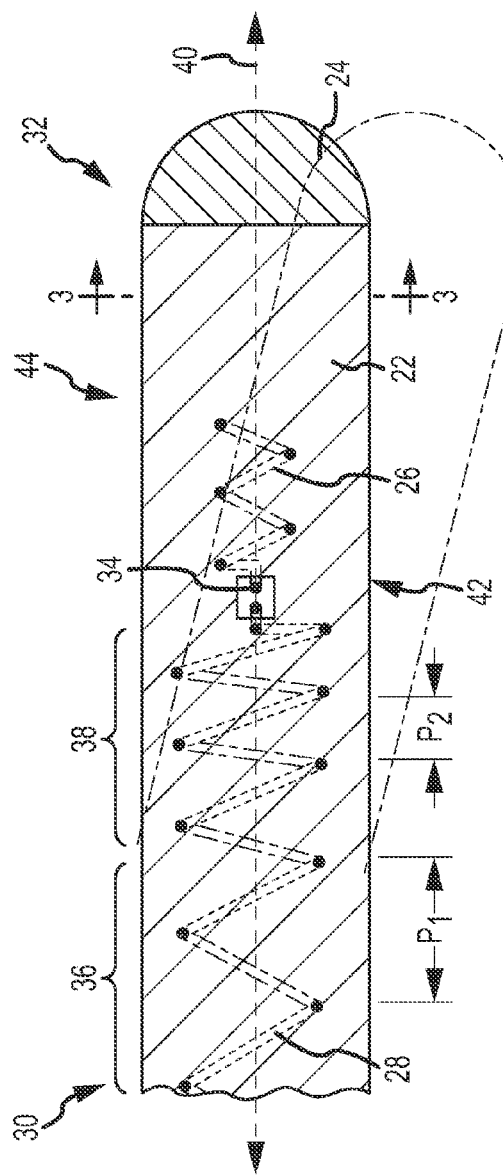
FIG. 2 is a cross-sectional view of a medical device in accordance with one embodiment of the present teachings.

Referring now to FIG. 2, one embodiment of a device 12 for treatment or diagnosis of tissue within body 14 in accordance with the present teachings is disclosed. Device 12 may comprise, for example, a catheter such as an electrophysiology (EP) mapping catheter, an ablation catheter or an intracardiac electrocardiography (ICE) catheter. Device 12 may include an elongate, deformable member 22, a medical operational element 24, a position sensor 26, and a conductor 28.

Member 22 is provided to transport element 24 to a region of interest and may comprise a catheter. Member 22 is an elongate, deformable (flexible) member configured to be received within, and to move within, a lumen within body 14 such as one of the lumens in the cardiovascular system, digestive system or the brain, liver, kidneys or lungs. Member 22 may support element 24, sensors 26, associated conductors 28, and possibly additional electronics used for signal processing or conditioning. Member 22 may also permit transport, delivery and/or removal of fluids (including irrigation fluids and bodily fluids), medicines, and/or surgical tools or elements.

Member 22 may be made from conventional materials such as poly ether ether ketone (PEEK), polyethylene (PE), nylon, polyurethane, polyvinyl chloride (PVC), polyethylene terephthalate (PET), the material sold under the trademark "PEBAX" by Arkema France, polyimide, metals (either solid or coiled) such as nitinol and stainless steel used in hypotubes (i.e., an ultra low diameter and ultra thin walled tubes) and the like. Member 22 may also have different mechanical properties along its length. For example, a compression coil may house the pull wires along a proximal portion of member 22. Portions of member 22 may also be made from materials having different durometers (e.g., a portion made having a relatively hard durometer in a proximal portion and a relatively soft durometer in a distal portion). Member 22 may be generally circular in cross-section and defines one or more lumens configured to house and/or transport electrical conductors 28, fluids, guidewires and surgical tools. Member 22 may be introduced into a blood vessel or other structure within the body through a conventional introducer sheath or another tubular body through which member 22 may be moved longitudinally. Member 22 may then be steered or guided through the body to a desired location with guide wires or other means known in the art. Member 22 has a proximal end 30 and a distal 32 end (as used herein, "proximal" refers to a direction toward the end of the catheter near the clinician, and "distal" refers to a direction away from the clinician and (generally) inside the body of a patient).

Element 24 is provided to perform an operation resulting in the diagnosis or treatment of tissue in body 14. Element 24 is disposed at distal end 32 of member 22. Element 24 may comprise any of a wide variety of conventional diagnostic and/or treatment instruments including those used to modify characteristics of tissues, diagnose tissues or generate images of tissues, including tissues found in body lumens. For example, element 24 may be used to vascularize a lumen, sever a portion of the lumen or plaque buildup on the lumen, provide a suture to a lumen or increase the size of the lumen (e.g., by a balloon, self expanding stent, a stent made of a shape memory alloy, or a balloon expanding stent) and maintain the increased diameter by implanting a stent and element 24 may therefore comprise a balloon, stent, or balloon expanding stent, for example. Element 24 may be used to deliver substances to the lumen such as a pharmacological substance. Element 24 may be used to create tissue necrosis by delivering ablation energy such as ultrasound energy, electromagnetic energy (e.g., radio frequency or lasers) or thermal energy (heat or cryo-ablation) and may therefore comprise a transducer, electrode, laser, or fluid delivery port or valve for example. Element 24 may also be used to deploy a device near a selected tissue such as a valve, marker or sensor. In the illustrated embodiment, element 24 is shown distal to sensor 26 at the distal tip of member 22. It should be understood, however, that the relative positions of element 24 and sensor 26 could vary. For example, element 24 could alternatively be radially aligned with sensor 26 where element 24 comprises a balloon, for example.

Position sensor 26 generates a position signal indicative of the position of sensor 26, and therefore device 12, within body 14. Sensor 26 is conventional in the art. In the illustrated embodiment, sensor 26 comprises a coil suitable for use with a position and navigation system 10 employing magnetic fields. As sensor 26 moves within body 14, and within the generated magnetic field, the current output of sensor 26 changes thereby indicating the location of sensor 26 within the magnetic field and with the coordinate system established by system 10. Sensor 26 may be wound about member 22 at or near distal end 32 and may be embedded within member 22 such that sensor 26 is insulated by member 22. Alternatively, sensor 26 could be embedded within member 22 laterally of the center of member 22 and not wound about member 22. Further, alternatively, sensor 26 could be external to member 22. Sensor 26 may also have appropriate insulation and/or shielding (e.g., a conductive foil or wire mesh) to cancel potential interferences from other devices near body 14. It should be understood that sensor 26 may take other forms other than the form illustrated in FIG. 2. Sensor 26 may, for example, comprise any conventional position sensors for detecting changes in magnetic fields including Hall effect sensors, magnetoresistive sensors and sensors made from magnetorestrictive materials and piezoelectric materials and the like. Sensor 26 may also, for example, comprise electrodes in systems employing electric fields to identify the position and orientation of sensors 26. Sensors 26 communicate position signals to ECU 18 through a conventional interface (not shown).

Conductors 28 are provided to transmit signals between ECU 18 and element 24 and between ECU 18 and sensors 26. Conductors 28 may comprise wires made from typical electrical conductors such as copper, gold or silver and the like or cables. Conductors 28 extend from elements 24 and sensors 26 to a point proximal to elements 24 and sensors 26 such as proximal end 30 of member 22. Conductors 28 are connected to elements 24 and sensors 26 at connection nodes such as node 34. Conductors 28 may be connected to elements 24 and sensors 26 directly through soldering or conductive adhesives or indirectly through a connector such as a flexible printed circuit board or wiring pad. Conductors 28 may extend to a connection interface at proximal end 30 of member 22 such that signals can be transmitted via another conductor to ECU 18. Alternatively, conductors 28 may terminate at a transmitter (not shown) within device 12 such that the information conveyed by conductors 28 is transmitted wirelessly to a corresponding receiver in system 10 connected to ECU 18.

Conductors 28 may be wound about member 22. Conductors 28 may be embedded within member 22 such that substantially the entire length of conductors 28 is surrounded or enclosed by the material forming member 22 and insulated by the material forming member 22. Conductors 28 may additionally be coated with a protective coating or coatings that provides electrical insulation and/or or electrical shielding as well as mechanical protection to conductors 28. Conductors 28 may alternatively be disposed within grooves formed in a radially outer surface of member 22 by a laser, mechanical engraving, chemical etching, molding, injection, extrusion or similar processes and covered with a protective coating or coatings to provide electrical insulation and/or electrical shielding as well as mechanical protection and to couple conductors 28 to the radially outer surface of member 22. Multiple conductors 28 to elements 24 or sensors 26 may be arranged in twisted pairs or coaxially as is known in the art.

In accordance with one embodiment of the present teachings, the pitch of conductor 28 may be varied along the longitudinal extent of conductor 28 and member 22. In other words, conductor 28 may have various winding pitches over different portions of member 22. In the embodiment shown in FIG. 2, for example, conductor 28 has one winding pitch $P_1$ over a portion 36 of member 22 nearer to the proximal end 30 of member 22 and a second winding pitch $P_2$ over a portion 38 of member 22 nearer to the distal end 32 of member 22. The winding pitch over a given portion of member 22 is preferably determined by the anticipated movement of different portions of member 22 and the different mechanical properties the manufacturer wishes to affect at each portion of member 22. The movement may be anticipated due to changes in the structure of member 22 by, for example, the termination of a compression coil, durometer changes in the member 22, pull ring locations, cross-sectional changes, or the like. The change in winding pitch for conductor 28 is located to work with these decision elements. Accordingly, the change in winding pitch may occur at the termination of a compression coil, the termination of a shape memory wire or other stiffener in member 22 or at a point at which the durometer of member 22 changes.

For example, the distal end 32 of member 22 may deflect from a straight line position relative to the rest of member 22 (i.e., be bent such that the distal tip of member 22 is drawn closer to the proximal end 30 of member 22) as shown in broken line in FIG. 2 in order to locate element 24 at an appropriate position and orientation relative to tissues in body 14 and/or to guide member 22 through body 14. As distal end 32 is deflected, conductor 28 will experience different compression and tension forces on different portions of conductor 28. Conductor 28 may be wound with a smaller winding pitch $P_2$ proximate distal end 32 to reduce these compression and tension forces. Conductor 28 may be wound with a greater winding pitch $P_1$ nearer to proximal end 30 where conductor 28 is not subject to the same mechanical stress. In this manner, the overall mechanical stress on conductor 28 is reduced. Further, various mechanical properties of member 22 may be improved including the increased pushability and traceability of member 22 (i.e., reducing the tendency of member 22 to buckle when pushed within the body lumen and increasing the ability of the member 22 to follow the vessel path), increased elasticity of member 22 (i.e., an increase in the tendency of member 22 to return to the original shape, after being deformed), increased modulus of elasticity of member 22 (i.e., an increase in the mechanical stress in either compression or tension, which is required to deform member 22 by a certain amount), increased coefficient of rigidity of member 22 (i.e., an increase in the mechanical shear stress which is required to twist member 22 by a certain angle), affecting the flexibility or resilience of member 22, and the like.

Figure 3:
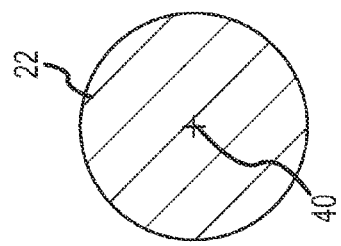
FIG. 3 is a cross-sectional view of the medical device of FIG. 2 taken along lines 3-3.

In accordance with another aspect of the present teachings, conductor 28 may be connected to a position sensor 26 at a connection node 34 that is disposed along a neutral axis 40 of member 22. Axis 40 is an axis along which there is no longitudinal stress or strain as member 22 is bent. For example, as distal end 32 of member 22 deflects from a straight line position as shown in broken line in FIG. 2, portions of member 22 on one side 42 of neutral axis 40 will be in a state of compression as the length of such portions is shortened whereas the portions of member 22 on the other side 44 of axis 40 will be in a state of tension as the length of such portions is increased. The length of neutral axis 40, however, will remain unchanged and is not subject to compression or tension. Because connection node 34 is located along neutral axis 40, connection node 34 is also not subjected to compression and tension forces and is less likely to be damaged. Referring to FIG. 3, axis 40 may be located at the geometric centroid of member 22.

Referring now to FIG. 4, another embodiment of a device 112 for treatment or diagnosis of tissue within body 14 in accordance with the present teachings is disclosed. Device 112 may include a tubular deformable member 122, a medical operational element 124, and a position sensor 126, and a conductor 128. Member 122, element 124, and sensor 16 may be substantially similar to member 22, element 24, and sensor 26, discussed hereinabove. Conductor 128 may also be substantially similar to conductor 28 discussed hereinabove. As opposed to being wound about member 122, however, conductor 128 may be coincident with neutral axis 140. Conductor 128 may extend from proximal end 130 to connection node 134 and may be coincident with neutral axis 140 along the entire length of conductor 128. In this manner, conductor 128 is not subject to compression and tension forces resulting from movement of member 122.

Referring now to FIG. 5, another embodiment of a device 212 for treatment or diagnosis of tissue within body 14 in accordance with the present teachings is disclosed. Device 212 may include a tubular deformable member 222, a medical operational element 224, and a position sensor 226, and a conductor 228. Member 222, element 224, and sensor 226 may be substantially similar to member 22, element 24, and sensor 26, discussed hereinabove. Conductor 228 may also be substantially similar to conductor 28 discussed hereinabove. As opposed to being wound about member 222 for its entire length, however, a portion 246 of a conductor 228 may extend along neutral axis 240 while another portion 248 of conductor 228 is wound about member 222. Portion 248 may again have varying winding pitches along different portions of member 222 for the purpose discussed hereinabove.

A medical device for diagnosis or treatment of a tissue within a body in accordance with the present teachings represents an improvement relative to conventional devices. In particular, by varying the pitch of the conductor and/or by locating portions of the conductor and/or the connection node from the conductor to the position sensor on the neutral axis of the device, mechanical stress on the conductors and connection nodes are reduced. As a result, the reliability and life of devices are improved.

Although several embodiments of this invention have been described above with a certain degree of particularity, those skilled in the art could make numerous alterations to the disclosed embodiments without departing from the scope of this invention. For example, although the illustrated embodiment shows a single medical device #, it should be understood that the system could be employed to determined the position and orientation of multiple medical devices as well as the relative positions of multiple medical devices. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A medical device configured for diagnosis or treatment of a tissue within a body, comprising:
    an elongate, deformable member configured to be received within a lumen in said body, having a proximal end and a distal end;
    a position sensor disposed at said distal end of said deformable member; and,
    a conductor wound about said deformable member, said conductor connected to said position sensor at a connection node, said conductor having a first winding pitch over a first portion of said deformable member and a second winding pitch over a second portion of said deformable member, said second winding pitch different from said first winding pitch.

2. The medical device of claim 1 wherein said second portion of said deformable member is distal to said first portion of said deformable member and said second winding pitch is smaller than said first winding pitch.

3. The medical device of claim 2 wherein the difference in said first and second winding pitches causes a change in a mechanical property of said deformable member.

4. The medical device of claim 3 wherein said change comprises an increase in said mechanical property and said mechanical property comprises flexibility.

5. The medical device of claim 1 wherein said position sensor comprises a coil.

6. The medical device of claim 5 wherein said coil is wound about said distal end of said deformable member.

7. The medical device of claim 1 further comprising a connector disposed at said connection node and connected to said position sensor and said conductor.

8. The medical device of claim 1 wherein said connection node is located on a neutral longitudinal axis extending between said proximal and distal ends of said member.

9. The medical device of claim 1 further comprising a compression coil disposed within said first portion of said deformable member.

10. The medical device of claim 1 further comprising:
   a plurality of pull wires disposed within said deformable member; and,
   a handle having a first actuator coupled to at least one pull wire of said plurality of pull wires.

11. The medical device of claim 1 wherein said first portion of said deformable member is made from a material having a first durometer and said second portion of said deformable member is made from a material having a second durometer, said second durometer less than said first durometer.

12. The medical device of claim 1 wherein said conductor is configured to transmit signals to or from said position sensor.

13. A medical device configured for diagnosis or treatment of a tissue within a body, comprising:
   an elongate, deformable member configured to be received within a lumen in said body, having a proximal end and a distal end, said deformable member defining a neutral longitudinal axis extending between said proximal and distal ends;
   a position sensor disposed at said distal end of said deformable member; and,
   a conductor extending between said proximal and distal ends of said deformable members, said conductor connected to said position sensor at a connection node on said neutral axis
   wherein said conductor has a first portion and a second portion, the second portion of said conductor having a first winding pitch over a first portion of said deformable member and a second winding pitch over a second portion of said deformable member, said second winding pitch different from said first winding pitch.

14. The medical device of claim 13 wherein only the first portion of said conductor is disposed on said neutral axis.

15. The medical device of claim 14 wherein the second portion of said conductor is wound about said deformable member.

16. The medical device of claim 15 where the second portion of said conductor is distal to said first portion of said conductor.

17. The medical device of claim 13 wherein said second portion of said deformable member is distal to said first portion of said deformable member and said second winding pitch is smaller than said first winding pitch.

18. The medical device of claim 13 wherein said position sensor comprises a coil.

19. The medical device of claim 18 wherein said coil is wound about said distal end of said deformable member.

20. The medical device of claim 13 further comprising a connector disposed at said connection node and connected to said position sensor and said conductor.

* * * * *